United States Patent [19]
Rosenbaum et al.

[11] Patent Number: 6,053,875
[45] Date of Patent: Apr. 25, 2000

[54] REMOVABLE TIP FOR AN ACOUSTIC REFLECTOMETER

[76] Inventors: Marvin Rosenbaum, Two Governor's Dr., Andover, Mass. 01810; Paul Bertram, 22 Catherine Ave., Franklin, Mass. 02038

[21] Appl. No.: 09/006,136

[22] Filed: Jan. 13, 1998

[51] Int. Cl.⁷ ..................................................... A61B 5/00
[52] U.S. Cl. .......................... 600/559; 73/585; 374/158
[58] Field of Search .................................. 600/559, 549; 374/158; 73/585; 396/342, 344, 529, 531

[56] References Cited

U.S. PATENT DOCUMENTS

| | | | |
|---|---|---|---|
| 3,559,542 | 2/1971 | Clapp | 95/44 |
| 3,848,950 | 11/1974 | McCormick et al. | 339/90 R |
| 4,056,298 | 11/1977 | Cooper et al. | 339/90 R |
| 4,183,605 | 1/1980 | Arneson | 339/89 M |
| 4,567,881 | 2/1986 | Heller | 128/9 |
| 4,601,295 | 7/1986 | Teele | 128/746 |
| 4,629,272 | 12/1986 | Mattingly et al. | 339/90 R |
| 4,687,071 | 8/1987 | Hartz et al. | 180/9.1 |
| 4,688,582 | 8/1987 | Heller et al. | 128/746 |
| 4,850,064 | 7/1989 | Cameron | 4/321 |
| 4,883,968 | 11/1989 | Hipple et al. | 250/423 R |
| 5,699,809 | 12/1997 | Combs et al. | 128/746 |

*Primary Examiner*—Cary O'Connor
*Assistant Examiner*—Charles Marmor, II
*Attorney, Agent, or Firm*—Alan W. Fiedler

[57] ABSTRACT

In one embodiment of the invention, the tip has a conical portion. Four connection tabs are orthogonally and evenly spaced on the outer circumference of the conical portion. The tip has a flange surrounding an outer circumference of the conical portion and parallel to the connection tabs. Between the connection tabs and the flange is a gap. The connection tabs and gap have a size such that they securely connect the tip of the acoustic reflectometer. The tip also may have a set of handling tabs connected between the flange and the conical section which simplify attachment of the tip to and removal of the tip from the acoustic reflectometer. The inner diameter of the tip has a shape that provides a matching acoustic impedance to the ear canal.

3 Claims, 9 Drawing Sheets

REMOVABLE TIP FOR AN ACOUSTIC REFLECTOMETER

FIELD OF THE INVENTION

The present invention is related to tips for medical devices. In particular, the present invention is related to removable and replaceable tips to be used with an acoustic reflectometer.

BACKGROUND OF THE INVENTION

Many medical devices have parts that are removable and replaceable if those parts are intended to be in direct contact with patients. An acoustic reflectometer, described, for example, in published PCT patent application WO96/23293, has a tip which is placed either adjacent to or into a patient's ear canal. Such a tip should be removable and replaceable.

The shape of the tip of an acoustic reflectometer may affect the acoustic impedance of the acoustic reflectometer and therefore may affect its measurements and any diagnosis made based on its measurements. Accordingly, the tip also should have both dimensions that provide a suitable acoustic impedance, and a mechanism that both securely connects the tip to the acoustic reflectometer and is easily removable.

SUMMARY OF THE INVENTION

In one embodiment of the invention, the tip has a conical portion. Four connection tabs are orthogonally and evenly spaced on the outer circumference of the conical portion. The tip has a flange surrounding an outer circumference of the conical portion and parallel to the connection tabs. Between the connection tabs and the flange is a gap. The connection tabs and gap have a size such that they securely connect the tip of the acoustic reflectometer. The tip also may have a set of handling tabs connected between the flange and the conical section which simplify attachment of the tip to and removal of the tip from the acoustic reflectometer. The inner diameter of the tip has a shape that provides a matching acoustic impedance to the ear canal.

DETAILED DESCRIPTION

The present invention will be more completely understood through the following detailed description which should be read in conjunction with the attached drawing in which similar reference numbers indicate similar structures.

Figure 1:
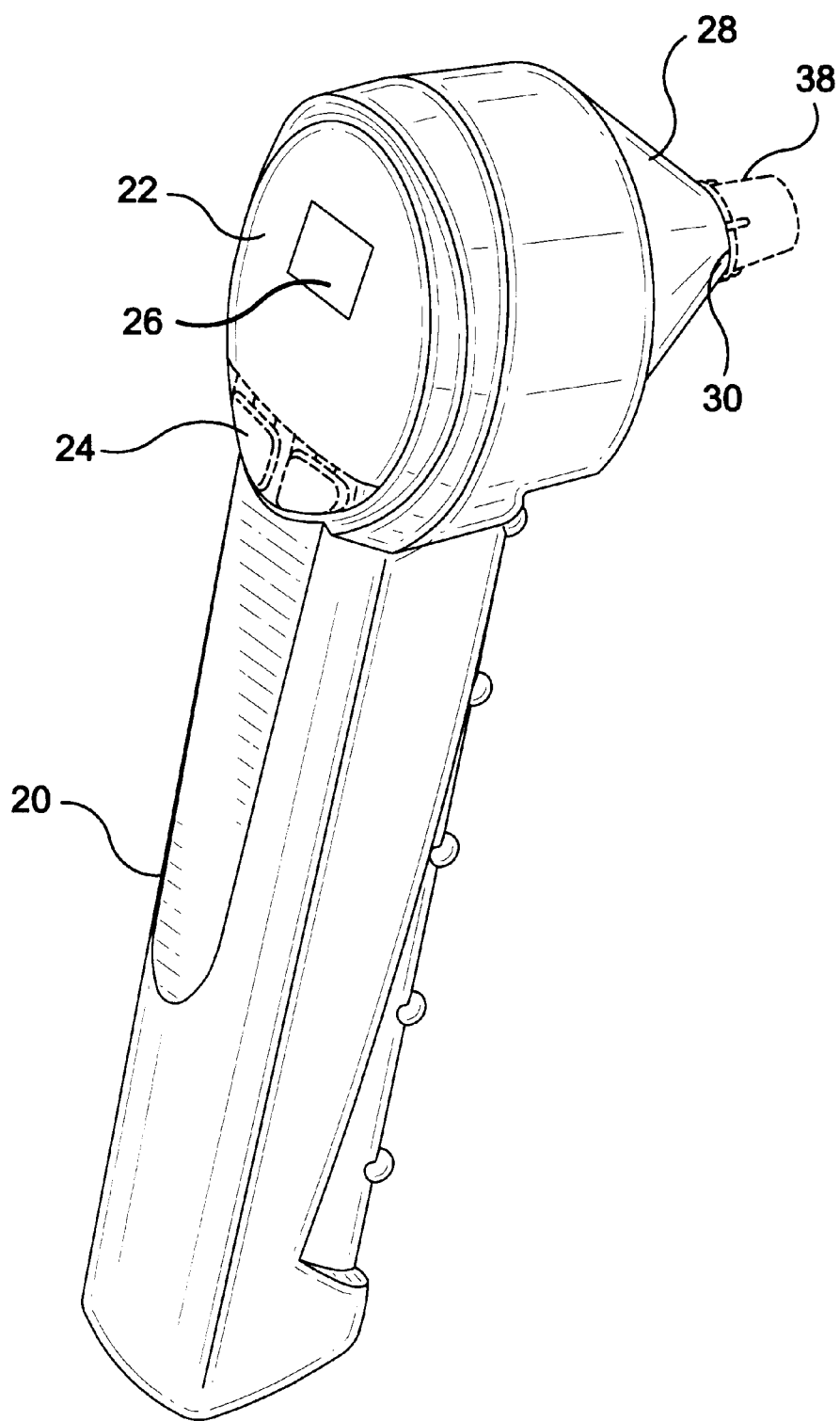
FIG. 1 is a perspective view of an example acoustic reflectometer with which the present invention may be used.

Referring now to FIG. 1, an example acoustic reflectometer is shown with which the present invention may be used. The acoustic reflectometer has a handle 20, allowing it to be held by an individual. A control panel 22 has one or more buttons 24 and a display 26 allowing the individual to operate the device and view results. In operation, the acoustic reflectometer generates an acoustic signal in an acoustic chamber 28 which is then directed through an opening 30 through a tip 38 and into the ear canal. Acoustic waves are reflected by the ear structures back through the tip and into the opening 30.

Figure 2:
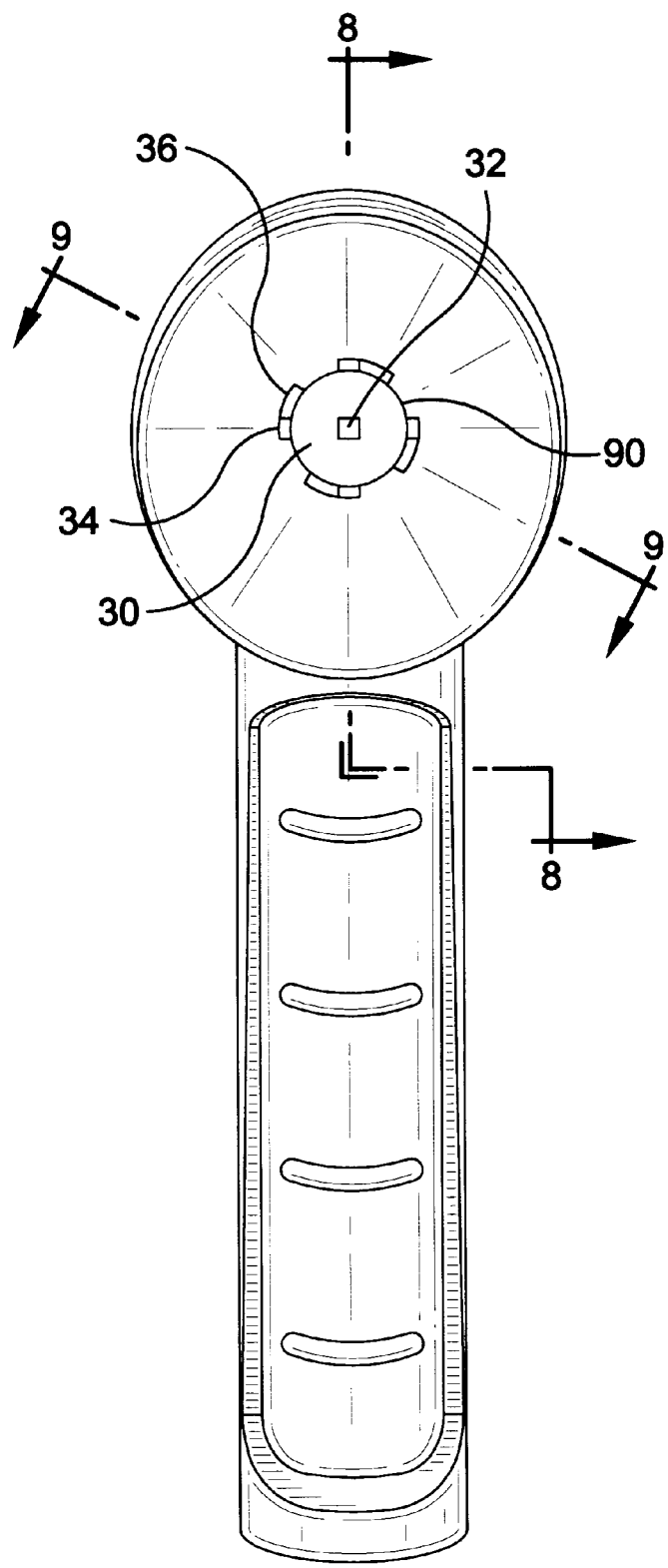
FIG. 2 is a plan view of an opening on an instrument for receiving the tip.

The opening 30 is shown in more detail in FIG. 2. The opening is circular and surrounds a microphone 32. The opening has four notches 34 which are orthogonally and evenly spaced about the opening. Adjacent each notch is a channel 36 beneath the surface 90 of device surrounding the opening. The channel 36 may receive a connection tab of a tip, in a manner to be described below.

Figure 3:
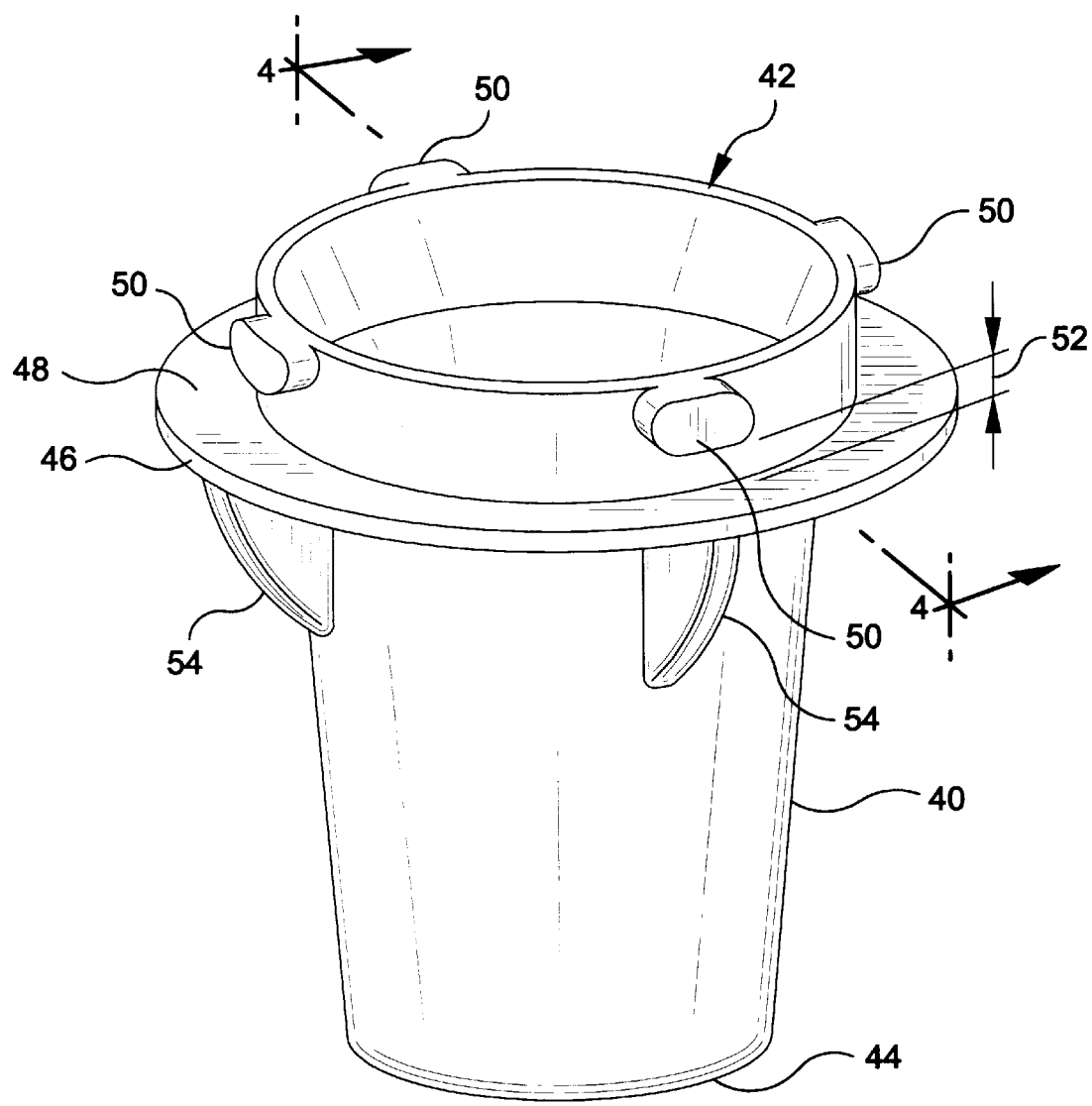
FIG. 3 is a perspective view of a tip in one embodiment of the present invention.

One embodiment of a removable tip is shown in FIG. 3. The tip has a conical portion 40. The inner diameter of the tip is larger at one end 42, called the base and which is connected to the acoustic reflectometer, than at another end 44, called the tip and which is adapted to be placed adjacent to or in the ear canal. The inner diameter affects acoustic impedance of the device and should provide an acoustic impedance match at frequencies within the primary range of operation of the acoustic reflectometer and particularly in the range of 1 to 5 kHz.

The conical portion 40 has a flange 46 which has a flat surface 48 on a side facing the acoustic reflectometer. At the base 42 of the conical portion, four connection tabs 50 are placed in an orthogonal relationship around the outer circumference. A gap 52 is formed between the tabs 50 and the flange 52. A set of handling connection tabs 54 also are placed about the conical portion 40, connected between the conical portion 40 and the flange 46. These handling tabs may be placed at the same positions around the conical portion 40 as the connection tabs 50.

Figure 4:
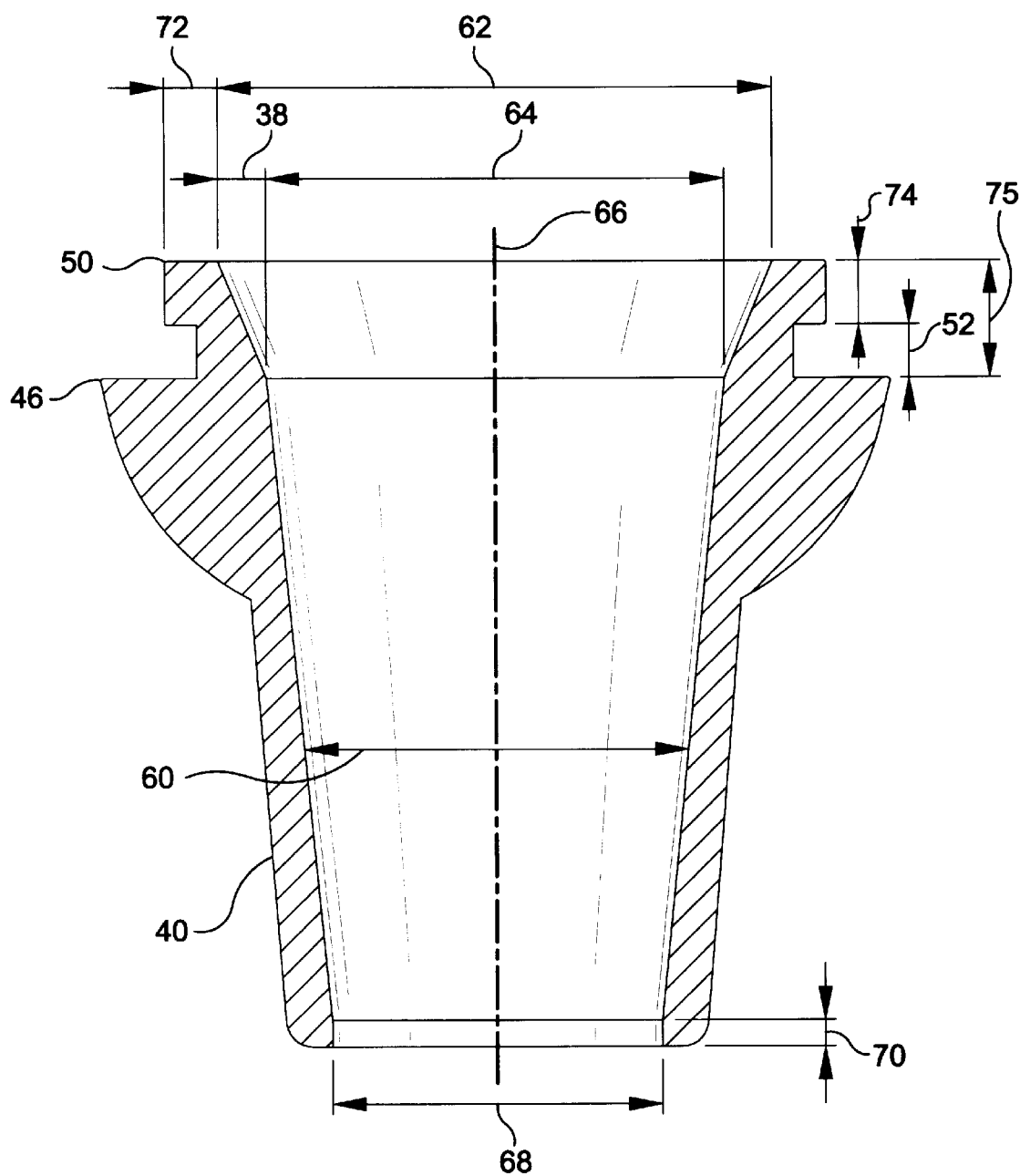
FIG. 4 is a cross-section of the tip along line 4—4 in FIG. 3.

FIG. 4 illustrates the cross-section of the removable tip along line 4—4 in FIG. 3. The tip has several dimensions which optimize the acoustic response for a given acoustic reflectometer. For example, the acoustic chamber of the EarCheck device available from MDI Instruments, Inc., is described in a 510(k) filing made to the Food and Drug Administration (See, 510(k) No. K970685). The inner diameter of the tip as shown at line 60 varies from the base of the tip that connects to the acoustic reflectometer to the opposite end of the tip which is placed adjacent to the ear canal. For the EarCheck device, the inner diameter 62, shown in FIG. 4, is 0.524 inches at the base. The inner diameter gradually decreases to 0.410 inches 64, shown in FIG. 4 over a length of 0.100 inches from the base along the axis 66 of the conical portion 40. For the EarCheck device, the inner diameter 68 at the tip is 0.305 inches. This diameter is constant over the last 0.025 inches of the tip as indicated at 70.

The tip also has a mechanism that securely connects the tip to the acoustic reflectometer. In particular, the connection tabs 50 have a length 72 and width (not shown) that are sufficient to fit within the notches 34 surrounding the opening 30 in the acoustic reflectometer. For example, the depth 74 of the notch may be approximately 0.050 inches. The gap 52 between the flange 46 and the tab 50 also may be approximately 0.050 inches. These dimensions 74 and 52, and their total length 75 also are dependent upon the depth at which the channel 36 begins below the surface 90 of the opening 30, as well as the total depth of the channel itself.

This relationship will be described in more detail below in connection with FIGS. 8 and 9.

Figure 5:
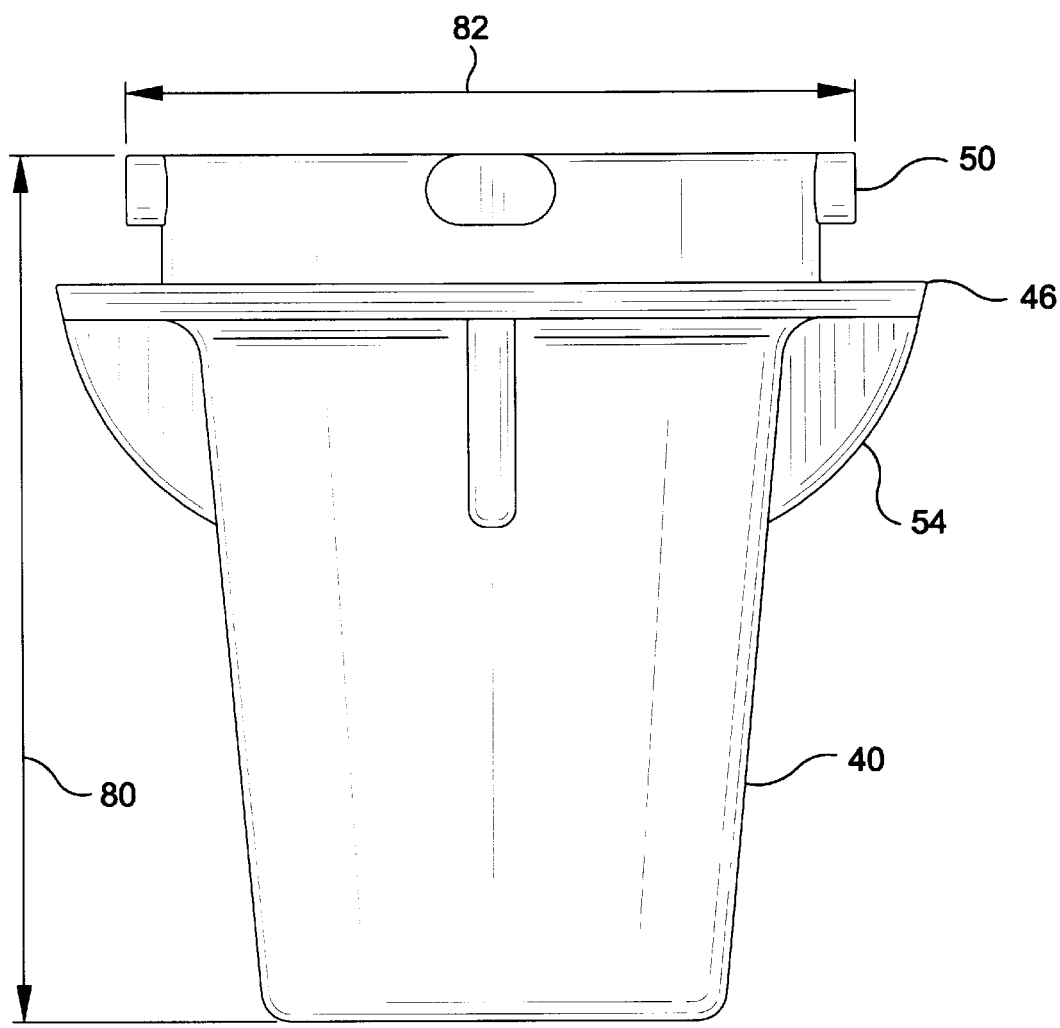
FIG. 5 is a side elevational view of the tip.

FIG. 5 is a side plan view of the removable tip from the same side as the cross-sectional diagram shown in FIG. 4. As shown in FIG. 5, for the EarCheck device, the overall length 80, shown in FIG. 5, of the tip is approximately 0.69 inches. The overall diameter 82, shown in FIG. 5, of the tip at the connection tabs 50 may be approximately 0.587 inches.

Figure 6:
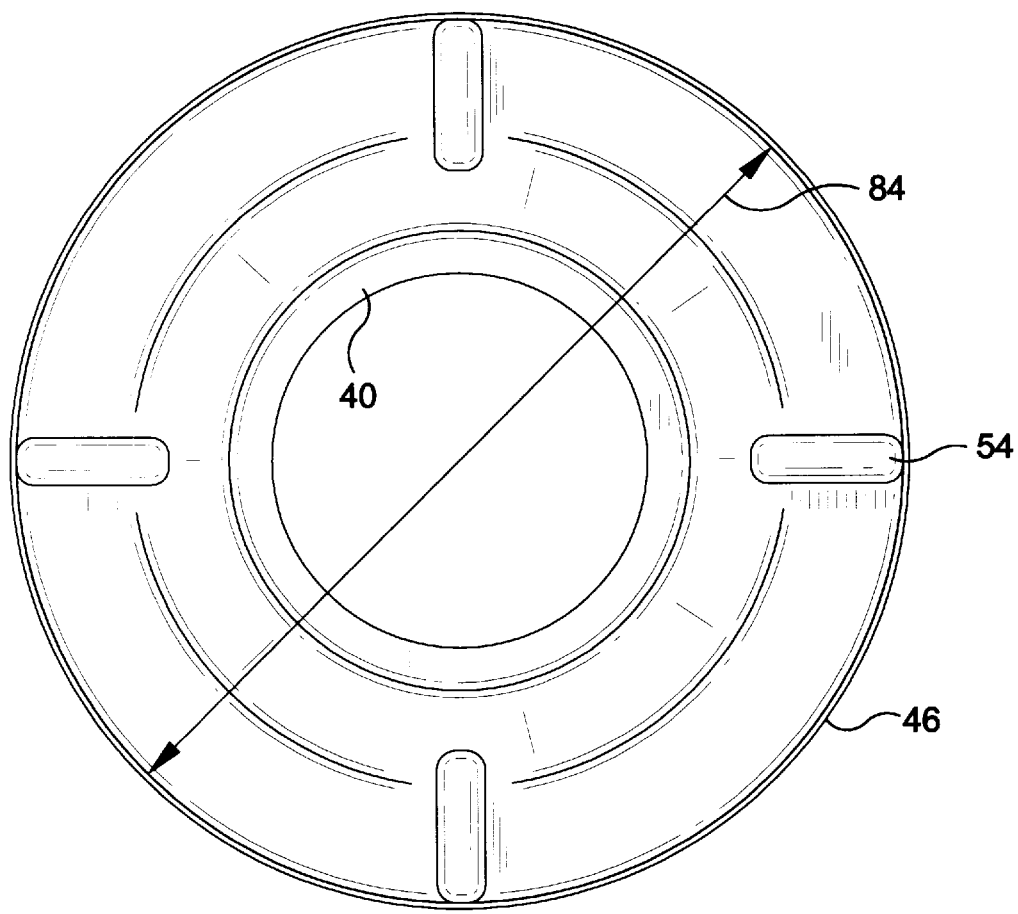
FIG. 6 is a top elevational view, from the end of the tip.

FIG. 6 illustrates a top plan view of the removable tip from the perspective of the tip, which is placed adjacent the ear canal. As can be seen, the handling tabs 54 are in an orthogonal relationship about the conical portion 40 and are connected to the flange 46. The overall diameter of the flange may be approximately 0.70 inches as indicated at 84.

Figure 7:
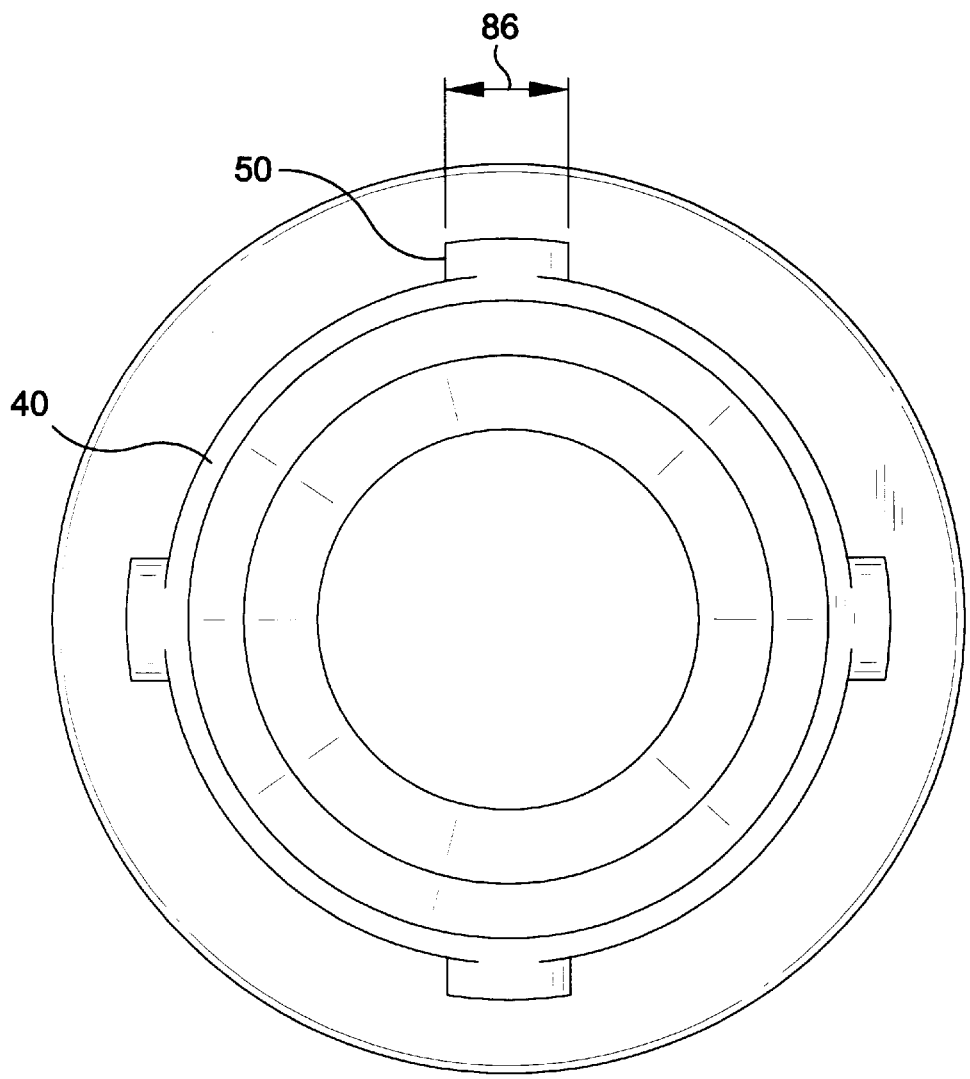
FIG. 7 is a bottom elevational view, illustrating the base of the tip.

FIG. 7 illustrates a bottom plan view of the removable tip, from the perspective of the base of the tip, which is connected to the acoustic reflectometer. As shown in FIG. 7, the connection tabs 50 are in an orthogonal relationship about the outer circumference of the conical portion 40. Each tab may be approximately 0.100 inches in length as shown at 86.

Figure 8:
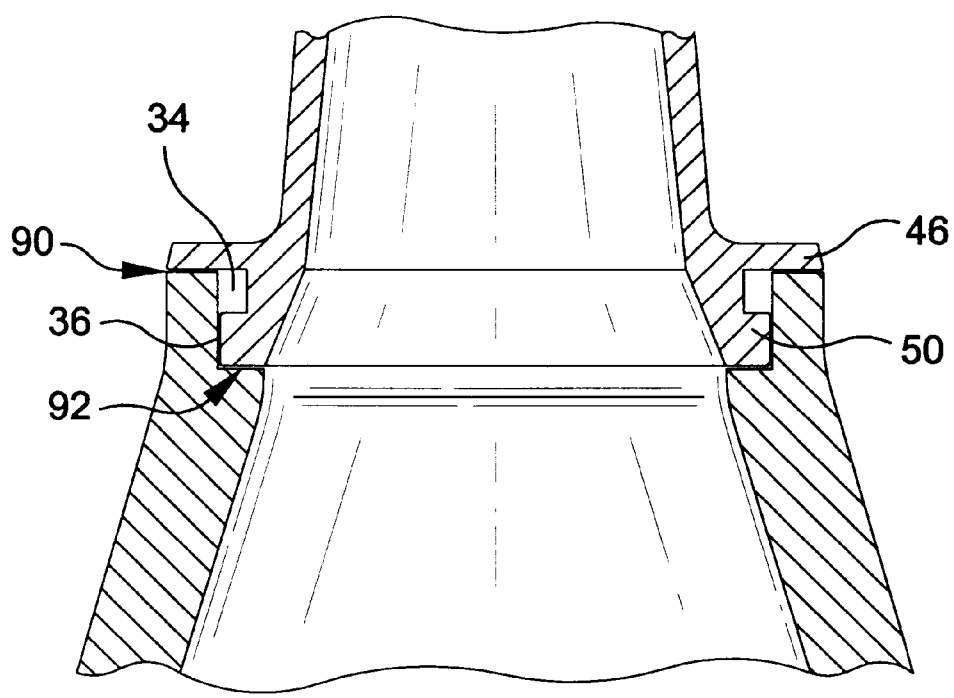
FIG. 8 is a cross-sectional diagram of the tip along line 8—8 of FIG. 2.

Referring now to FIG. 8, the connection of the tip to the acoustic reflectometer will be shown. FIG. 8 shows a cross-section of the acoustic reflectometer through line 8—8 in FIG. 2 along with a tip inserted into the notches on the device. One of the connection tabs 50 on the removable tip is shown inserted into a notch 34 such that the flange 46 is flush against the surface 90 of the acoustic reflectometer about the opening 30. The base of the tip is supported by the base of the opening, shown at 92, so that a smooth transition is formed from the acoustic chamber to the inner diameter of the tip.

Figure 9:
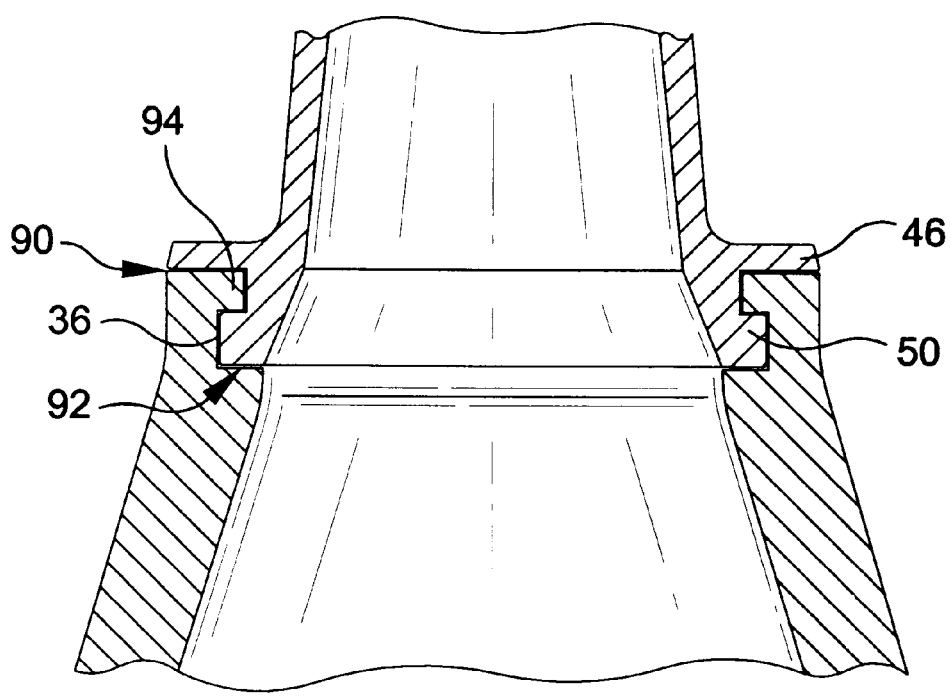
FIG. 9 is a cross-sectional diagram of the tip along line 9—9 of FIG. 2.

The individual rotates the tip so that the connection tabs 50 enter into channels 36, as shown in FIG. 9 (which is a cross-section through line 9—9 in FIG. 2). The top of the channel 94 which is defined by the surface 90 of the opening 30, fits in the gap 52 between the flange 46 in connection tabs 50. The tight tolerances between the gap 52 and top of the channel 94, between the connection tab 50 and the channel 36 between the flange 46 and the base 92 of the acoustic reflectometer securely connects the removable tip to the acoustic reflectometer.

Such a tip may be made of plastic through any common molding or extrusion process. Suitable plastic is polyethylene 7791, low density. The removable tip may be designed such that twisting of the tip via the handling tabs 48 causes discoloration. A material, such as a polymer, that changes structure and color in response to twisting may be incorporated into the plastic tip for this purpose. Discoloration of a tip indicates that the tip was already used. This capability is desirable since such tips should be used only once in any clinical or hospital setting.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims and equivalent thereto.

What is claimed is:

1. A tip for an acoustic reflectometer, said tip comprising:

an element having a circular cross section about a major axis, an outer circumference, and an overall length of approximately 0.69 inches to provide a matching acoustic impedance between an acoustic reflectometer and an ear canal;

four orthogonally and evenly spaced connection tabs on the outer circumference of said element; and a flange surrounding the outer circumference of said element and parallel to a circle defining the location of said connection tabs, and defining a gap between said connection tabs and said flange.

2. The tip of claim 1, wherein said element has a conical shape and a base with an inner diameter of 0.410 inches and an open end having an inner diameter of 0.305 inches.

3. The tip of claim 1, further comprising a plurality of handling tabs connected to said flange and to said element.

* * * * *